United States Patent
Sakai et al.

(10) Patent No.: US 12,374,461 B2
(45) Date of Patent: Jul. 29, 2025

(54) INFORMATION PROCESSING DEVICE, INFORMATION PROCESSING METHOD, AND RECORDING MEDIUM

(71) Applicant: NEC Corporation, Tokyo (JP)

(72) Inventors: Tomoya Sakai, Tokyo (JP); Hiroshi Tamano, Tokyo (JP)

(73) Assignee: NEC CORPORATION, Tokyo (JP)

( * ) Notice: Subject to any disclaimer, the term of this patent is extended or adjusted under 35 U.S.C. 154(b) by 145 days.

(21) Appl. No.: 18/037,510

(22) PCT Filed: Nov. 25, 2020

(86) PCT No.: PCT/JP2020/043814
§ 371 (c)(1),
(2) Date: May 17, 2023

(87) PCT Pub. No.: WO2022/113203
PCT Pub. Date: Jun. 2, 2022

(65) Prior Publication Data
US 2024/0038389 A1    Feb. 1, 2024

(51) Int. Cl.
*G16H 50/20* (2018.01)

(52) U.S. Cl.
CPC .................................. *G16H 50/20* (2018.01)

(58) Field of Classification Search
None
See application file for complete search history.

(56) References Cited

U.S. PATENT DOCUMENTS

| | | | |
|---|---|---|---|
| 2005/0102145 A1* | 5/2005 | Shiomi | G10L 17/26 704/E17.002 |
| 2020/0010137 A1 | 1/2020 | Komemushi | |
| 2020/0010144 A1 | 1/2020 | Kondo | |
| 2020/0010148 A1 | 1/2020 | Shimazu et al. | |

(Continued)

FOREIGN PATENT DOCUMENTS

| | | | |
|---|---|---|---|
| JP | 2014-048795 A | 3/2014 |
| JP | 2019-016279 A | 1/2019 |

(Continued)

OTHER PUBLICATIONS

Scherer, Towards a Prediction and Data Driven Computational Process Model of Emotion, IEEE Transactions on Affective Computing, vol. 12, No. 2, Apr.-Jun. 2021.*

(Continued)

*Primary Examiner* — David J Stoltenberg

(57) ABSTRACT

In the strange feeling prediction device, the prediction result acquisition means inputs diagnosis data to a target prediction model which is a trained prediction model serving as a target, and acquires a prediction result by the target prediction model. The label acquisition means acquires a strange feeling label indicating a strange feeling of an expert with respect to the prediction result. The strange feeling prediction model training means trains a strange feeling prediction model using the prediction result and the strange feeling label. The strange feeling prediction means outputs a strange feeling index indicating the strange feeling with respect to the prediction result outputted by the target prediction model, using the trained strange feeling prediction model.

7 Claims, 7 Drawing Sheets

(56) References Cited

U.S. PATENT DOCUMENTS

| | | | |
|---|---|---|---|
| 2020/0010149 A1 | 1/2020 | Shimazu et al. | |
| 2020/0012964 A1 | 1/2020 | Shimazu et al. | |
| 2020/0014321 A1 | 1/2020 | Kondo | |
| 2020/0014322 A1 | 1/2020 | Kondo | |
| 2020/0090067 A1* | 3/2020 | Anders | G06F 18/214 |
| 2020/0126664 A1 | 4/2020 | Sato | |
| 2020/0242842 A1* | 7/2020 | Fukazawa | G06T 7/11 |
| 2021/0012244 A1* | 1/2021 | Taniguchi | G06N 20/20 |
| 2021/0398676 A1* | 12/2021 | Evans | G06N 3/08 |
| 2023/0045696 A1* | 2/2023 | Griffin | G06N 20/00 |
| 2023/0105659 A1* | 4/2023 | Banerjee | G06V 10/7715 |
| | | | 702/19 |

FOREIGN PATENT DOCUMENTS

| | | | | | |
|---|---|---|---|---|---|
| JP | 2019-204484 A | | 11/2019 | | |
| JP | 2020-006836 A | | 1/2020 | | |
| JP | 2021-18821 A | * | 7/2020 | | G05B 23/02 |
| WO | WO 2020/241009 A1 | * | 3/2020 | | G06N 20/00 |

OTHER PUBLICATIONS

Bouktif, et al. Ant Colony Optimization Algorithm for Interpretable Bayesian Classifiers Combination: Application to Medical Predictions, PLOS ONE | www.plosone.org Feb. 1, 2014 | vol. 9 | Issue 2 | e86456.*

International Search Report for PCT Application No. PCT/JP2020/043814, mailed on Jan. 12, 2021.

Abe et al., "A Rule Evaluation Support Method with Learning Models Based on Objective Rule Evaluation Indexes", ICDM'05, pp. 1-4, 2005 IEEE.

Abe et al., "Evaluating a Rule Evaluation Support Method Based on Objective Rule Evaluation Indices—A Case Study on a Chronic Hepatitis Data Mining Result-", 72th SIG-KBS, JSAI, 2006, pp. 67-72.

Abe et al., "A Comparison between Clustering Algorithms based on Objective Rule Evaluation Indices and Human Subjective Criteria", 21st Annual Conference of JSAI, 2007, pp. 1-2, 3F6-1.

JP Official Communication for JP Application No. 2022-564882, mailed on Apr. 16, 2024 with English Translation.

* cited by examiner

<TRAINING OF TRAGET PREDICTION MODEL>

<TRAINING OF STRANGE FEELING PREDICTION MODEL>

<EVALUATION OF STRANGE FEELING>

INFORMATION PROCESSING DEVICE, INFORMATION PROCESSING METHOD, AND RECORDING MEDIUM

This application is a National Stage Entry of PCT/JP2020/043814 filed on Nov. 25, 2020, the contents of all of which are incorporated herein by reference, in their entirety.

TECHNICAL FIELD

The present invention relates to technology of incorporating an expert's knowledge into prediction using artificial intelligence.

BACKGROUND ART

In making various predictions using artificial intelligence, an attempt has been made to incorporate knowledge of experts in that field. For example, Patent Document 1 describes a technique of incorporating knowledge of an expert in a medical field into a diagnostic system using artificial intelligence.

PRECEDING TECHNICAL REFERENCES

Patent Document

Patent Document 1: Japanese Patent Application Laid-Open under No. 2019-204484

SUMMARY

Problem to Be Solved by the Invention

Experts in each field often make appropriate judgments and predictions by using empirical rules cultivated in that field. Therefore, it can be expected that predictions and judgment close to experts can be made by successfully incorporating experts' empirical rules into predictions and judgment using AI (Artificial Intelligence).

It is an object of this invention to provide an information processing device capable of generating an evaluation index based on empirical rules of experts for prediction results by a prediction model using AI.

Means for Solving the Problem

According to an example aspect of the present invention, there is provided an information processing device comprising:
  a prediction result acquisition means configured to input diagnosis data to a target prediction model which is a trained prediction model serving as a target, and acquire a prediction result by the target prediction model;
  a label acquisition means configured to acquire a strange feeling label indicating a strange feeling of an expert with respect to the prediction result;
  a strange feeling prediction model training means configured to train a strange feeling prediction model using the prediction result and the strange feeling label: and
  a strange feeling prediction means configured to output a strange feeling index indicating the strange feeling with respect to the prediction result outputted by the target prediction model, using the trained strange feeling prediction model.

According to another example aspect of the present invention, there is provided an information processing method comprising:
  inputting diagnosis data to a target prediction model which is a trained prediction model serving as a target, and acquiring a prediction result by the target prediction model;
  acquiring a strange feeling label indicating a strange feeling of an expert with respect to the prediction result;
  training a strange feeling prediction model using the prediction result and the strange feeling label: and
  outputting a strange feeling index indicating the strange feeling with respect to the prediction result outputted by the target prediction model, using the trained strange feeling prediction model.

According to still another example aspect of the present invention, there is provided a recording medium recording a program, the program causing a computer to:
  input diagnosis data to a target prediction model which is a trained prediction model serving as a target, and acquire a prediction result by the target prediction model;
  acquire a strange feeling label indicating a strange feeling of an expert with respect to the prediction result;
  train a strange feeling prediction model using the prediction result and the strange feeling label: and output a strange feeling index indicating the strange feeling with respect to the prediction result outputted by the target prediction model, using the trained strange feeling prediction model.

EXAMPLE EMBODIMENTS

Preferred example embodiments of the present invention will be described with reference to the accompanying drawings.

Basic Principle

Experts in each field often make appropriate judgement and prediction by using empirical rules. Therefore, the expert feels strange for the prediction result, when the prediction result obtained using AI greatly deviates from his own empirical rule. For example, if the prediction result by AI shows that there will be a large demand that the experts in the field (hereinafter also referred to as "domain experts") cannot explain well, or if the prediction result visualized will deviate from the trends of time series, the domain experts feel strange for the prediction results by AI.

Figure 1:
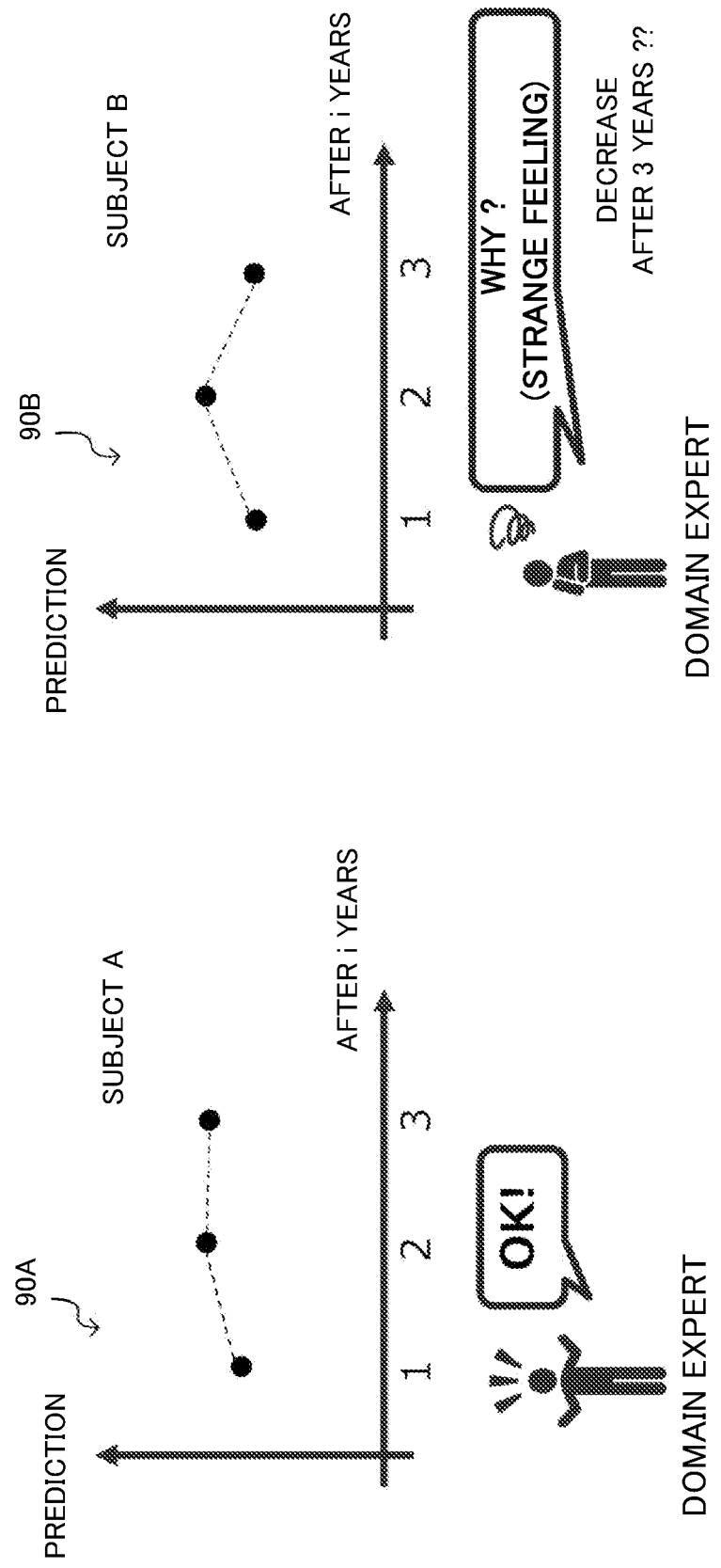
FIG. 1 shows an example of prediction result that domain experts feel strange.

FIG. 1 shows an example of prediction result for which domain experts feel strange. It is supposed that there is a model which predicts future body fat rate in time series using AI based on a present body fat rate and life habits of the subject. If the body fat rate is expected to increase as the present lifestyle is continued, the domain experts will not feel strange when the AI model outputs the prediction result 90A in which the body fat rage tends to increase as a whole, as shown in the left side of FIG. 1. On the other hand, if the AI model outputs the prediction result 90B in which the body fat rate largely increases or decreases at any point in time, as shown in the right side of FIG. 1, the domain experts feel strange because the prediction 90B does not conform to the empirical rules of the domain experts.

It can be expected that prediction and judgment close to experts will become possible if the experts' empirical rules and/or the strange feeling based on the empirical rules can be successfully incorporated in the prediction and the judgment using AI. Therefore, in the following example embodiments, a strange feeling prediction model is generated to the predict presence or absence of the strange feeling or the degree of the strange feeling that the domain experts have for the prediction result of AI, and the strange feeling prediction model is used to output an index (hereinafter, also referred to as "a strange feeling index") indicating the presence or absence of the strange feeling or the degree of the strange feeling for the prediction result of AI.

The resulting strange feeling index can be used to generate a prediction model when developing AI. For example, the strange feeling index can be used as an index in selecting an appropriate model from multiple models, or the strange feeling index can be incorporated into the training algorithm of the model. It is also possible to utilize the strange feeling index as a monitoring index in the actual operation of AI. For example, it is possible to output an alert according to the value of the strange feeling index during operation of the system. In this way, AI systems that incorporate the empirical rules of domain experts can be realized.

First Example Embodiment

Device for Evaluating Strange Feeling

Figure 2:
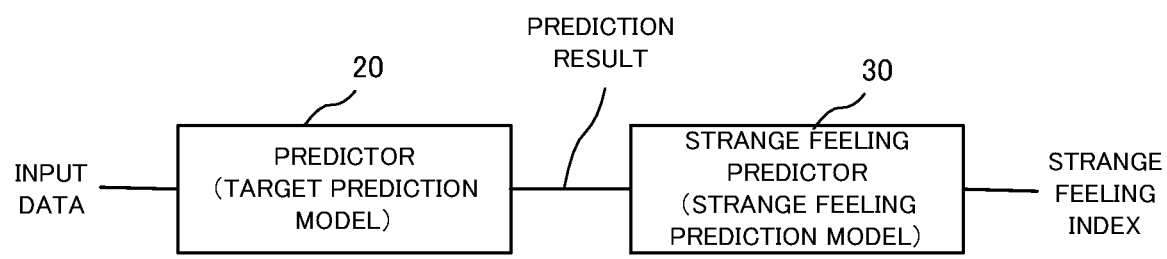
FIG. 2 is a block diagram showing a schematic configuration of a strange feeling evaluation device according to a first example embodiment.

FIG. 2 is a block diagram showing a schematic configuration of a strange feeling evaluation device according to the first example embodiment. The strange feeling evaluation device 100 outputs the strange feeling index for a prediction result outputted by a prediction model to be evaluated (hereinafter, also referred to as "target prediction model"). Specifically, the strange feeling evaluation device 100 includes a predictor 20 using the target prediction model and a strange feeling predictor 30 using the strange feeling prediction model. The target prediction model is a prediction model corresponding to the task to be solved. The predictor 20 performs prediction based on the input data, and outputs the prediction result to the strange feeling predictor 30. For example, when the task to be solved is the prediction of the body fat rate as described above, the input data is information such as the present body fat rate and life habits of the subject, and the predictor 20 outputs a predicted value of the future body fat rate based on the input data.

The strange feeling prediction model is a model that evaluates the strange feeling of the domain experts on the prediction result of the predictor 20. The strange feeling predictor 30 outputs the strange feeling index indicating the strange feeling of the domain experts for the prediction result by the predictor 20. Here, the strange feeling index may be a numerical value indicating the strange feeling (e.g., a value between "0" and "1"), or may be a function for calculating a numerical value indicating the strange feeling.

Hardware Configuration

Figure 3:
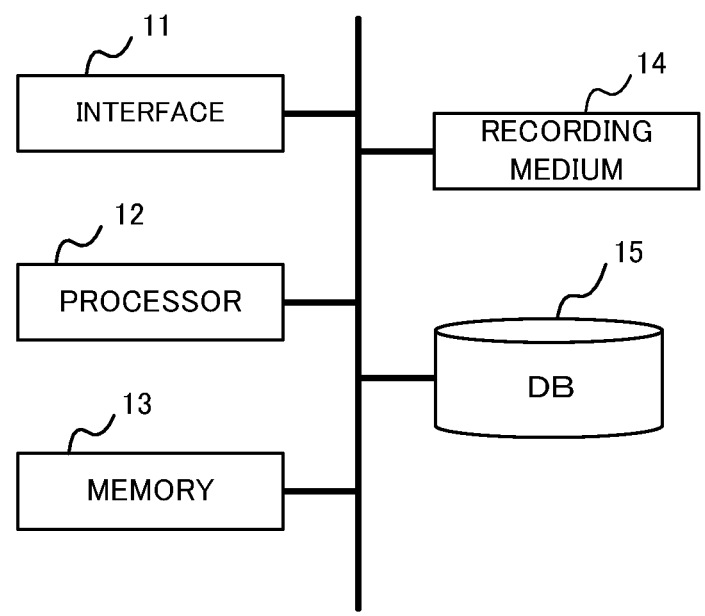
FIG. 3 is a block diagram showing a hardware configuration of the strange feeling evaluation device.

FIG. 3 is a block diagram showing a hardware configuration of the strange feeling evaluation device 100. As illustrated, the strange feeling evaluation device 100 includes an interface 11, a processor 12, a memory 13, a recording medium 14, and a data base (DB) 15.

The interface 11 inputs and outputs data to and from external devices. Specifically, the interface 11 receives input data that the predictor 20 uses for prediction, training data used for training the strange feeling prediction model, or the like from the outside. Also, the interface 11 is used to output the strange feeling index generated by the strange feeling evaluation device 100 to an external device.

The processor 12 is a computer such as a CPU (Central Processing Unit) and controls the entire strange feeling evaluation device 100 by executing a program prepared in advance. The processor 112 may be a GPU (Graphics Processing Unit) or a FPGA (Field-Programmable Gate Array). Specifically, the processor 12 executes strange feeling evaluation processing to be described later.

The memory 13 may be a ROM (Read Only Memory) and a RAM (Random Access Memory). The memory 13 is also used as working memory during various processing by the processor 12.

The recording medium 14 is a non-volatile and non-transitory recording medium such as a disk-like recording medium or a semiconductor memory and is configured to be detachable from the strange feeling evaluation device 100. The recording medium 14 records various programs executed by the processor 12. When the strange feeling evaluation device 100 executes the processing, the program recorded in the recording medium 14 is loaded into the memory 13 and executed by the processor 12.

The DB 15 stores input data, training data, and the like inputted through the interface 11. The strange feeling evaluation device 100 may further include a display device and an input device for a user to perform necessary instruction input and setting.

Evaluation of Strange Feeling

In evaluating the strange feeling by the strange feeling evaluation device 100, the followings are prepared.

(a) Training data

This training data is used for training the target prediction model.

(b) Predictors

The predictor 20 using the target prediction model, and the strange feeling predictor 30 using the strange feeling prediction model are prepared.

(c) Domain expert

Domain experts are basically humans and are the experts in that field (domain), e.g., medical doctors in the medical field. The domain experts may be operators experienced in the operation of AI in that domain.

(d) Method of presenting the prediction result by the target prediction model to the domain experts (e) Strange feeling diagnosis data Strange feeling diagnosis data is data prepared by the method of (d), i.e., the data produced by the method of presenting the prediction result to the domain experts.

In the present example embodiment, the evaluation of the strange feeling for the prediction result of the predictor 20 is performed by three steps of: (1) training the target prediction model, (2) training the strange feeling prediction model, and (3) evaluating the strange feeling using the strange feeling prediction model. Each step will be described in order below.

(1) Training the Target Prediction Model

Figure 4:
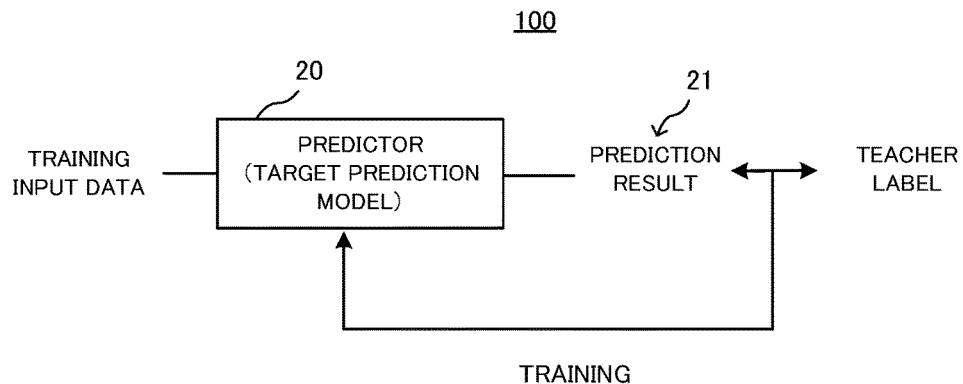
FIG. 4 schematically shows a method of training a target prediction model.

FIG. 4 schematically illustrates a method of training a target prediction model. Training of the target prediction model used in the predictor 20 is performed by so-called supervised learning, and training data prepared in advance are used. The training data includes training input data and teacher labels indicating correct answers to the training input data. At the time of training, the training data prepared in advance is inputted to the predictor 20. The predictor 20 uses the target prediction model corresponding to the task of interest as described above. Specifically, as the target prediction model, a model using a neural network or a model for other machine learning can be used, for example. The predictor 20 outputs the prediction result for the training input data. The prediction result is compared with the teacher label prepared in advance, and the target prediction model is trained based on the error (loss). When the predetermined training end condition is satisfied, training of the target prediction model is ended, and the trained target prediction model is obtained.

(2) Training the Strange Feeling Prediction Model

Figure 5:
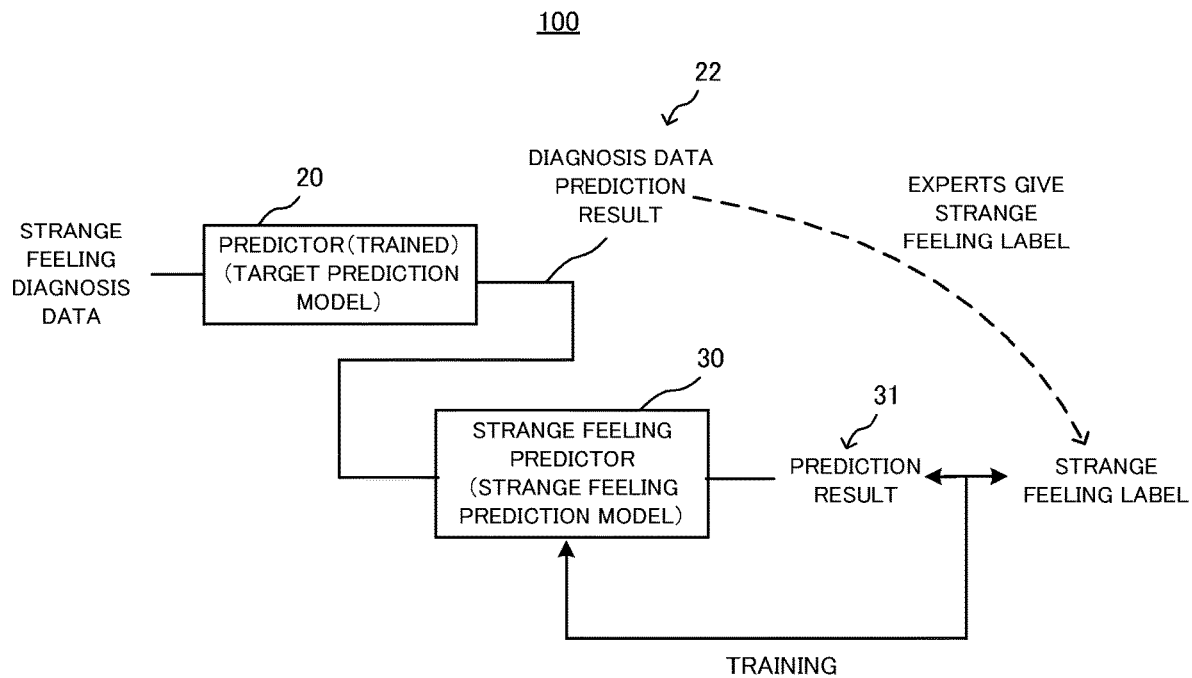
FIG. 5 schematically shows a method of training a strange feeling prediction model.

FIG. 5 schematically illustrates a method of training a strange feeling prediction model. Training of the strange feeling prediction model used in the strange feeling predictor 30 is also performed by so-called supervised learning. In the training of the strange feeling prediction model, first, the strange feeling diagnosis data is inputted to the trained predictor 20. The strange feeling diagnosis data is data created by a predetermined method for presenting the prediction result by the predictor 20 to the domain experts.

The trained predictor 20 performs prediction for the strange feeling diagnosis data and outputs the prediction result to the strange feeling predictor 30. In addition, the prediction result of the predictor 20 for the strange feeling diagnosis data (hereinafter, also referred to as "diagnosis data prediction result") is presented to the domain experts. The domain experts give strange feeling labels indicating the presence/absence or the degree of the strange feeling to the diagnosis data prediction result. The strange feeling labels correspond to the teacher labels created by the domain experts.

The strange feeling prediction model is a model for evaluating the strange feeling of the prediction result of the predictor 20, and may be a model using a neural network or machine learning. The strange feeling predictor 30 performs prediction based on the inputted diagnosis data prediction result, and outputs a prediction result 31. The prediction result 31 outputted by the strange feeling predictor 30 is compared with the strange feeling label provided by the domain experts, and the strange feeling prediction model is trained based on the error (loss). Then, when the predetermined training end condition is satisfied, the training of the strange feeling prediction model is ended, and the trained strange feeling prediction model is obtained.

For example, in the case of predicting the body fat rate shown in FIG. 1, training of the strange feeling prediction model is performed using the predicted values of the body fat rate of the subject after 1 to 3 years. Therefore, as the strange feeling diagnosis data, data for predicting the body fat rate of the subject after 1 to 3 years using the target prediction model is used. For example, the present fat body rates, the numerical values (height, weight, etc.) used for the prediction of the body fat rate, the life habits of the subject, and the like for multiple subjects are used as the strange feeling diagnosis data. The predictor 20 performs prediction of the body fat rate on the basis of these strange feeling diagnosis data, and outputs the predicted values of the body fat rate of the subject after 1 to 3 years as the diagnosis data prediction result 22.

The predicted body fat rate values of the subjects after 1 to 3 years are presented to the domain experts as the diagnosis data prediction results 22. The domain experts determine whether or not there is a strange feeling as shown in FIG. 1 based on the predicted values of the body fat rate of the subjects after 1 to 3 years, and give the strange feeling labels to the diagnosis data prediction results 22. The strange feeling prediction model is trained by using the diagnosis data prediction results 22 as the inputs and using the strange feeling labels given by the domain experts as the teacher labels. Thus, when the predicted values of the body fat rate of the subjects after 1 to 3 years are inputted from the predictor 20, the trained strange feeling prediction model can evaluate the strange feeling of the predicted values with a sense close to the domain experts.

(3) Evaluation of Strange Feeling

Figure 6:
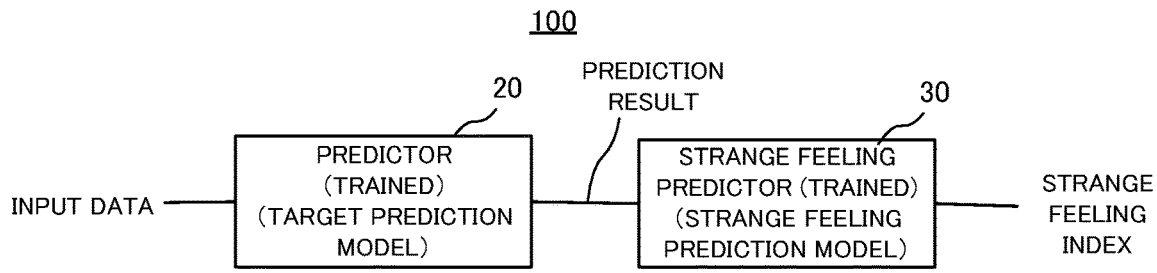
FIG. 6 schematically shows a method of evaluating the strange feeling.

FIG. 6 schematically shows a method of evaluating the strange feeling. When evaluating the strange feeling, the predictor 20 using the trained target prediction model and the strange feeling predictor 30 using the trained strange feeling prediction model are used. The input data is inputted to the predictor 20. Similar to the strange feeling diagnosis data described above, the input data is such data that the predictor 20 outputs a prediction result conforming to the input to the trained strange feeling predictor 30. For example, in the above-described example of predicting the body fat rate, the input data is the data that makes the predictor 20 output a predicted value of the body fat rate of a certain subject after 1 to 3 years. The predictor 20 performs prediction based on the input data, and outputs the prediction result to the strange feeling predictor 30. The strange feeling predictor 30 predicts the strange feeling for the inputted prediction result and outputs the strange feeling index. Thus, the strange feeling for the prediction result of the predictor 20 is evaluated.

In the above-described configuration, the predictor 20 is an example of a prediction result acquisition means and an target prediction model training means. The strange feeling predictor 30 is an example of a label acquisition means, a strange feeling prediction model training means, and an strange feeling prediction means.

Strange Feeling Evaluation Processing

Figure 7:
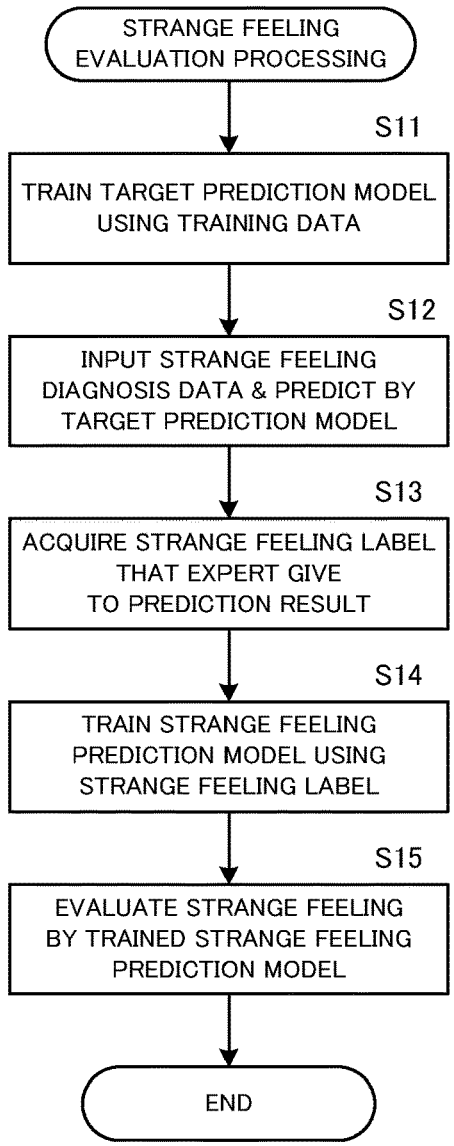
FIG. 7 is a flowchart of strange feeling evaluation processing according to the first example embodiment.

Next, the strange feeling evaluation processing including the above three steps will be described. FIG. 7 is a flowchart of the strange feeling evaluation processing according to the first example embodiment. This processing is realized by the processor shown in FIG. 3, which executes a program prepared in advance.

First, as shown in FIG. 4, the strange feeling evaluation device 100 trains the target prediction model using the training data (step S11). Thus, the predictor 20 that uses the trained target prediction model is obtained. Next, as shown in FIG. 5, the strange feeling evaluation device 100 inputs the strange feeling diagnosis data to the predictor 20, and the predictor 20 generates diagnosis data prediction results (step S12). The generated diagnosis data prediction results are inputted to the strange feeling predictor 30.

Also, the generated diagnosis data prediction results are presented to the domain experts, and the strange feeling labels are given by the domain experts. The strange feeling evaluation device 100 acquires the strange feeling labels given by the domain experts (step S13) and trains the strange feeling prediction model using the diagnosis data prediction results and the strange feeling labels (step S14). Thus, the strange feeling predictor 30 using the trained strange feeling prediction model is obtained.

When the predictor 20 using the trained target prediction model and the strange feeling predictor 30 using the trained strange feeling prediction model are obtained, the strange feeling evaluation device 100 evaluates the strange feeling for the actual prediction result as shown in FIG. 6. That is, the strange feeling evaluation device 100 inputs the input data to the predictor 20, and inputs the prediction result by the predictor 20 to the strange feeling predictor 30, thereby to evaluate the strange feeling (step S15). The strange feeling predictor 30 outputs the strange feeling index as the evaluation result of the strange feeling. Thus, the strange feeling for the prediction result of the predictor 20 is evaluated.

In the flowchart of FIG. 7, for convenience of explanation, a series of processes are included. However, when the training of the target prediction model has already been completed, it is sufficient to simply acquire the trained target prediction model, instead of step S11. Further, when the above-described strange feeling evaluation processing is used at the time of developing the model using AI, basically, as shown in the flowchart of FIG. 7, the strange feeling prediction model is trained in the step S14, and then the strange feeling is evaluated using the strange feeling prediction model in step S15. On the other hand, when the strange feeling evaluation processing is used during the actual operation of the model using AI, the process of evaluating the strange feeling in step S15 is repeated while updating the strange feeling prediction model in step S14.

Specific Example of Evaluating Strange Feeling

Next, a specific example of evaluating the strange feeling will be described.

(1) Training the Target Prediction Model

First, a predictor given by Equation (1) is used as the target prediction model. The target prediction model g receives a d-dimensional real number vector as an input and outputs a real number prediction value.

[Formula 1]

$$\mathcal{G} \ni g: \mathbb{R}^d \to \mathbb{R} \tag{1}$$

Equation (2) is used as the training data. In the training data D, $x_i$ is the training input data, $y_i$ is the teacher label, and n is the number of data.

[Formula 2]

$$\mathcal{D} = \{(x_i, y_i)\}_{i=1}^{n}$$

where $x \in \mathbb{R}^d, y \in Y$ \hfill (2)

The training of the target prediction model g is performed using training data D. The training of the target prediction model g is expressed by the following Equation (3).

[Formula 3]

$$\hat{g} = \underset{g \in \mathcal{G}}{\operatorname{argmin}} \frac{1}{n} \sum_{i=1}^{n} \hat{\ell}(g(x_i), y_i) + \tilde{\lambda} \tilde{W}(g) \tag{3}$$

where $\hat{\ell}: R \times y \to \mathbb{R}_{\geq 0}$ $\tilde{W}: \mathcal{G} \to \mathbb{R}_{\geq 0}$ $\tilde{\lambda} \geq 0$ Where $\ell$ denotes the loss, $\lambda$ denotes the regularization parameter, and $W(g)$ denotes the regularization function.

(2) Training the Strange Feeling Prediction Model

The strange feeling diagnosis data D' shown below is used.

[Formula 4]

$$\mathcal{D}' = \{D'_j\}_{j=1}^{n'} \tag{4}$$

Specifically, the following partial strange feeling diagnosis data $D'_j$ is extracted from the strange feeling diagnosis data D' and inputted to the trained predictor 20. Here, "n'" is the number of the partial strange feeling diagnosis data.

[Formula 5]

$$\mathcal{D}'_j = \{x_{i,j}'\}_{i=1}^{b} \tag{5}$$

Where "b" is the number of the prediction results presented to the domain experts for one partial strange feeling diagnosis data. Incidentally, the partial strange feeling diagnosis data $D'_j$ may be different from the training data D, and may be made from the training data D.

The prediction results of the predictor 20 for the strange feeling diagnosis data $D'_j$ are presented to the domain experts as the following b-dimensional vector z.

[Formula 6]

$$z: \mathcal{D} \times \mathcal{G} \to \mathbb{R}^b \tag{6}$$

For example, in a case where b prediction results are presented for each partial strange feeling diagnosis data $D'_j$, the following diagnosis data prediction results $z_j$ are presented to the domain experts.

[Formula 7]

$$z_j := (z_{1,j}, \ldots, z_{b,j})^\tau = z(\mathcal{D}'_j, \hat{g})$$

where $z_{i,j} := \hat{g}(x_{i,j}')$ \hfill (7)

Specifically, first the partial strange feeling diagnosis data $D'_j$ is inputted to the predictor 20. The predictor 20 performs the prediction using the trained prediction model $\hat{g}$ and generates the diagnosis data prediction results $z_j$ shown by Equation (7) for the partial strange feeling diagnosis data $D'_j$.

The diagnosis data prediction results $z_j$ are presented to the domain experts, and the strange feeling labels are given by the domain experts. The strange feeling labels thus given are shown by Equation (8).

[Formula 8]

$$\{(z_j, s_j)\}_{j=1}^{n'} \tag{8}$$

For example, if the presence of the strange feeling is expressed by "1" and the absence of the strange feeling is expressed by "0", the strange feeling label "s" is expressed as "$s \in \{0, 1\}$".

The diagnosis data prediction results $z_j$ and the strange feeling labels $s_j$ thus obtained are used to train the following strange feeling prediction model h.

[Formula 9]

$$\mathcal{H} \ni h: \mathbb{R}^b \to \mathbb{R} \tag{9}$$

The training of the strange feeling prediction model h is shown by the following equation.

[Formula 10]

$$\hat{h} := \underset{h \in \mathcal{H}}{\operatorname{argmin}} \frac{1}{n'} \sum_{j=1}^{n'} \ell(h(z_j), s_j) + \lambda W(h) \tag{10}$$

where $\ell: \mathbb{R} \times \{0, 1\} \to \mathbb{R}_{\geq 0}$
$W: \mathcal{H} \to \mathbb{R}_{\geq 0}$
$\lambda \geq 0$ Incidentally, $\ell$ denotes the loss, $\lambda$ denotes the regularization parameter, and W(h) denotes the regularization function. The strange feeling prediction model h is trained so that the sum of the average of the losses $\ell$ and the regularization term is minimized. Thus, the trained strange feeling prediction model h^ is obtained.

Figure 8:
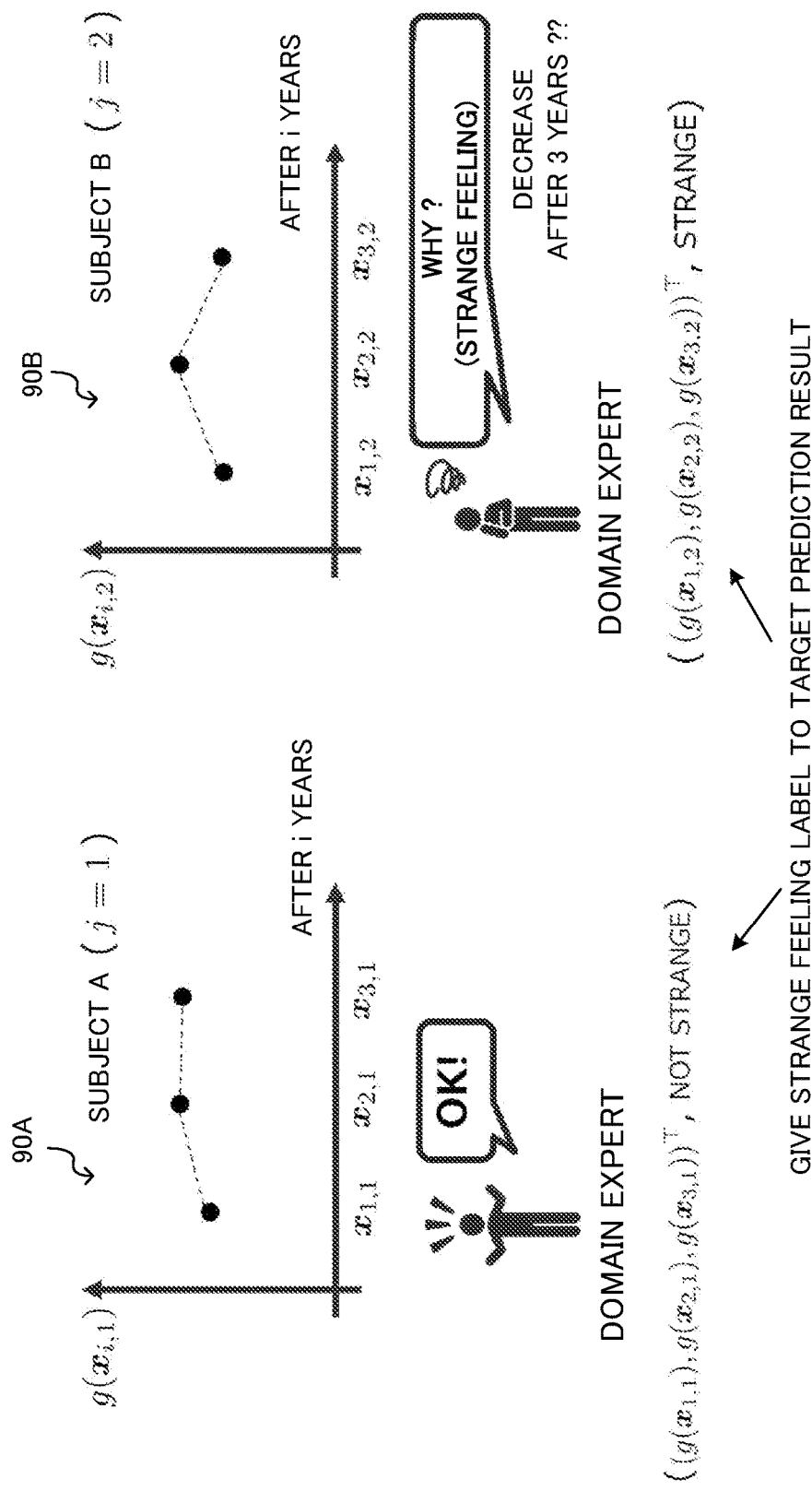
FIG. 8 shows an example of applying evaluation of strange feeling to body fat rate prediction based on life habits.

Here, an example of giving the strange feeling label will be described. FIG. 8 shows an example in which the strange feeling evaluation by the strange feeling evaluation device 100 is applied to the prediction of the body fat rate based on the life habits. As shown in FIG. 8, as the partial strange feeling diagnosis data $D'_j$,

[Formula 11]

$$D'_j = \{x_{ij}'\}_{i=1}^b \tag{11}$$

is used, and as the diagnosis data prediction results z,

[Formula 12]

$$z(\mathcal{D}'_j, g) = (g(x_{ij}'), \ldots, g(x_{ij}'))^\tau \tag{12}$$

are adopted. It is assumed that the prediction results outputted by the target prediction model are for 1 to 3 years (i.e., b=3), and the target subjects are A (j=1) and B (j=2).

In this case, as shown in FIG. 8, the prediction results 90A for the subject A are $g(x_{1,1})$ for one year later, $g(x_{2,1})$ for two years later, and $g(x_{3,1})$ three years later, and the domain expert gives the strange feeling labels indicating that there is no strange feeling. On the other hand, the prediction result 90B for the target B are $g(x_{1,2})$ for one year later, $g(x_{2,2})$ for two years later, and $g(x_{3,2})$ for three years later, and the domain expert gives the strange feeling labels indicating that there is a strange feeling. Thus, the strange feeling prediction model is trained to output the strange feeling index that matches the sense of the domain expert.

(3) Evaluating the Strange Feeling Using the Strange Feeling Prediction Model

The strange feeling predictor 30 outputs the strange feeling index using the strange feeling diagnosis data D' and the trained strange feeling prediction model h^. Examples of the strange feeling index are as follows.

First Example

In the first example, the strange feeling diagnosis data D' is fixed, and the target prediction model g is changed to calculate the strange feeling index $S_1(g; D')$ by the following Equation (13).

[Formula 13]

$$S_1(g; \mathcal{D}') := \frac{1}{n'} \sum_{j=1}^{n'} \hat{h}(z(\mathcal{D}'_j, g)) \tag{13}$$

Second Example

In the second example, the trained target prediction model g^ is fixed, and the strange feeling diagnosis data D" shown in Equation (14) is changed to calculate the strange feeling index $S_2(D"; g^)$ using the following Equation (15).

[Formula 14]

$$\mathcal{D}'' = \{\mathcal{D}''_j\}_{j=1}^{n''} \tag{14}$$

[Formula 15]

$$S_2(D''; \hat{g}) = \frac{1}{n''} \sum_{j=1}^{n''} \hat{h}(z(D''_j, \hat{g})) \tag{15}$$

The Third Example

In the third example, softmax function is applied to the strange feeling prediction model h^ as shown in Equation (16) and the output is converted into the range of "0" to "1" in the first example.

[Formula 16]

$$\hat{h}'(x) = \operatorname{softmax}(\hat{h})(x) \tag{16}$$

Then, the following Equation (17) is used to calculate the strange feeling index $S_3(g; D')$.

[Formula 17]

$$S_3(g; \mathcal{D}') := \frac{1}{n'} \sum_{j=1}^{n'} \hat{h}'\left(z(\mathcal{D}'_j, g)\right) \tag{17}$$

Usage Examples of the Strange Feeling Index

Next, usage examples of the strange feeling index will be described.

(1) In Case of Using the Strange Feeling Index as it is

For example, when using the strange feeling index for the target prediction model g in actual operation, the strange feeling index $S_2(g; D")$ shown in Equation (18) is used.

[Formula 18]

$$S_2(g; \mathcal{D}'') := \frac{1}{n''} \sum_{j=1}^{n''} \hat{h}(z(\mathcal{D}''_j, g)) \tag{18}$$

Namely, the target prediction model g that is currently in operation is fixed, and the strange feeling diagnosis data D" obtained during the operation is used to calculate the strange feeling index $S_2(g; D")$. Thus, the fitting degree of the target prediction model g to the domain is evaluated.

On the other hand, when using the strange feeling index during the development or training of the prediction model, the above Equation (18) and the following Equation (19) are used.

[Formula 19]

$$\hat{j} := \underset{1 \leq j \leq m}{\arg\min} S_2(\hat{g}_j; \mathcal{D}'') \quad (19)$$

Namely, the strange feeling diagnosis data D" is fixed, and the strange feeling index $S_2(g\hat{}_j; D'')$ is calculated for multiple candidates of the target prediction model using Equation (20).

[Formula 20]

$$\{\hat{g}_j\}_{j=1}^m \quad (20)$$

Then, a target prediction model suitable for the sense of the domain experts is selected from the multiple candidates of the target prediction model.

(2) In Case of Using the Strange Feeling Index to Train the Prediction Model

After step S15 in the flowchart of FIG. 7, the process of training the target prediction model g using the strange feeling index is executed. At that time, a regularization term using the strange feeling index according to the previous Equation (17) is provided, and the target prediction model g is trained so that the strange feeling is reduced by the following Equation (21).

[Formula 21]

$$\hat{g}_2 = \underset{g \in \mathcal{G}}{\arg\min} \frac{1}{n} \sum_{i=1}^{n} \ell(g(x_i), y_i) + \mu S_3(g; \mathcal{D}') \quad (21)$$

Modification

For the first example embodiment described above, it is possible to apply the following modifications. The following modifications can be applied in combination as required.

Modification 1

In the first example embodiment, the prediction result by the target prediction model for the strange feeling diagnosis data is presented to the domain experts to give the strange feeling labels. However, this work becomes a burden for the domain experts. Therefore, in Modification 1, active learning is utilized to reduce the burden of the strange feeling labeling work performed by the domain experts. In this case, it is possible to apply various techniques of active learning.

Hereinafter, an example of utilizing active learning will be specifically described. First, as an initialization process, the strange feeling evaluation device 100 uses the trained predictor 20 to generate, from the strange feeling diagnosis data $$\{D_j'\}_{j=1}^{n'} \quad \text{[Formula 22]}$$

the diagnosis data prediction result $$\{z_j\}_{j=1}^{n'} \quad \text{[Formula 23]}$$

in advance. Next, the strange feeling evaluation device 100 collects the strange feeling labels given by the domain experts to the diagnosis data prediction results $z_j$ sampled k randomly. Next, the strange feeling evaluation device 100 trains the strange feeling prediction model using the diagnosis data prediction results $z_j$ and the collected k strange feeling labels. Thus, the initialization process ends.

Next, the strange feeling evaluation device 100 selects the strange feeling diagnosis data with low confidence in prediction by the strange feeling prediction model trained in the initialization process. In this case, it is possible to select the strange feeling diagnosis data using various criteria according to the technique of active learning to be adopted. Next, the strange feeling evaluation device 100 presents the diagnosis data prediction result outputted by the target prediction model for the selected strange feeling diagnosis data to the domain experts and acquires the strange feeling labels. Then, the strange feeling evaluation device 100 updates the strange feeling prediction model using the acquired strange feeling labels. The strange feeling evaluation device 100 repeats the process until a predetermined end condition is satisfied, and outputs the strange feeling index using the strange feeling prediction model at the time when the end condition is satisfied.

Figure 9:
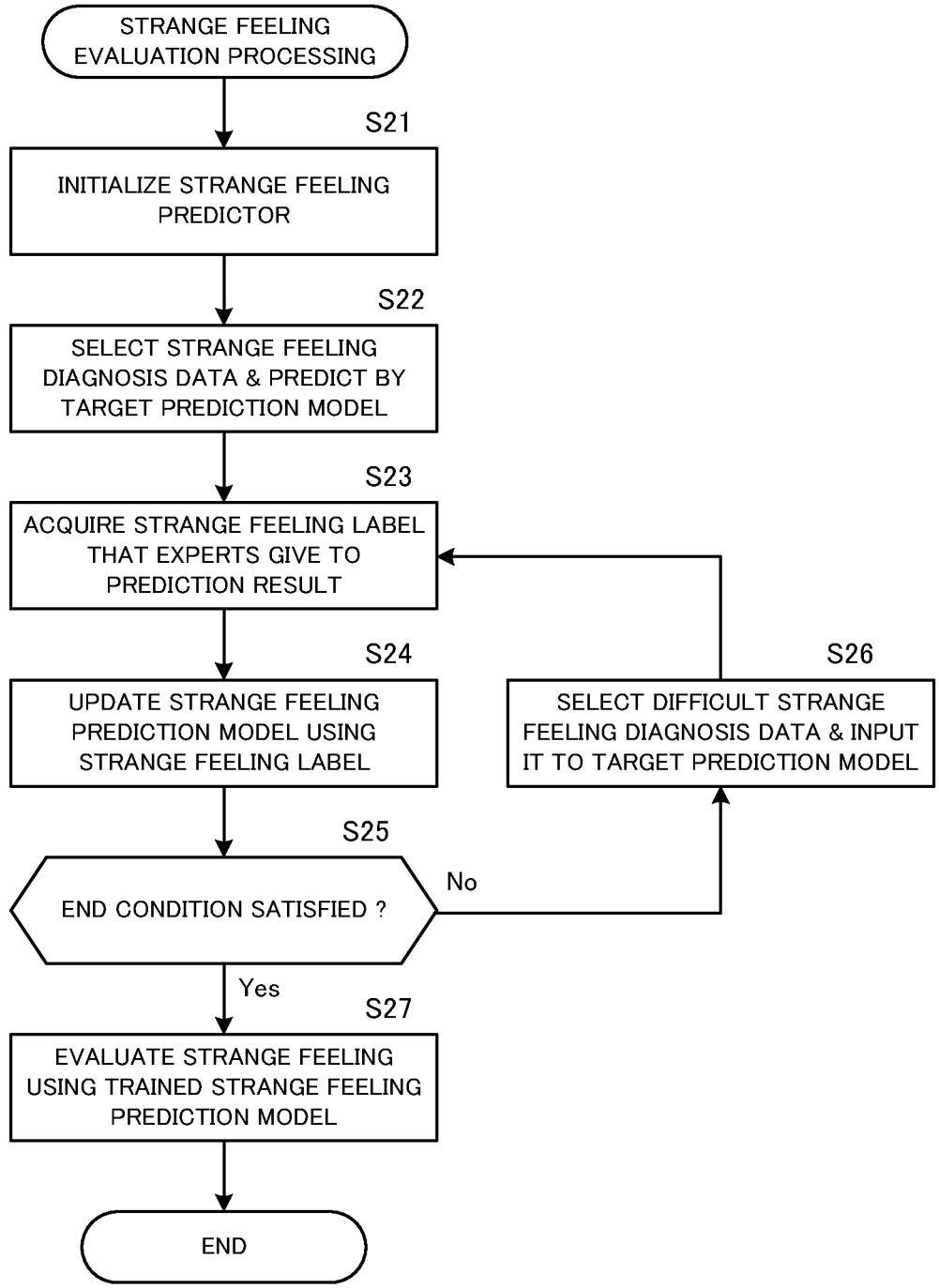
FIG. 9 is a flowchart of strange feeling evaluation processing in the case of applying an active learning to the application of the strange feeling label.

FIG. 9 is a flowchart of the strange feeling evaluation processing in the case where the active learning is applied to the application of the strange feeling labels. As a premise, it is assumed that the target prediction model has already been trained. First, the strange feeling evaluation device 100 performs the initialization process of the strange feeling predictor described above (step S21). Next, the strange feeling evaluation device 100 selects one of the strange feeling diagnosis data, inputs it to the trained predictor 20, and generates a diagnosis data prediction result using the target prediction model (step S22).

The generated diagnosis data prediction result is inputted to the strange feeling predictor 30. In addition, the generated diagnosis data prediction result is presented to the domain expert, and the strange feeling label is given by the domain expert.

Next, the strange feeling evaluation device 100 acquires the strange feeling label given by the domain expert (step S23), and updates the strange feeling prediction model using the diagnosis data prediction result and the strange feeling label (step S24). Next, the strange feeling evaluation device 100 determines whether or not a predetermined end condition is satisfied (step S25). Here, the predetermined end condition is, for example, that the update of the strange feeling prediction model was performed using a predetermined number or more of the strange feeling labels, or that the strange feeling diagnosis data for which determination of the strange feeling by the strange feeling predictor 30 is difficult is no longer found, and the like.

If the end condition is not satisfied (step S25: No), the strange feeling evaluation device 100 selects one or more of the strange feeling diagnosis data for which determination of the strange feeling by the strange feeling predictor 30 is difficult, and inputs the data to the predictor 20 (step S26). Then, the strange feeling evaluation device 100 repeats steps S23 to S25. On the other hand, when the end condition is satisfied (step S25: Yes), the strange feeling evaluation device 100 ends the training of the strange feeling prediction model. Then, the strange feeling evaluation device 100 performs evaluation of the strange feeling for the actual prediction result, as shown in FIG. 6. That is, the strange feeling evaluation device 100 inputs the input data to the predictor 20, and inputs the prediction result by the target prediction model to the strange feeling predictor 30. Thus, the strange feeling evaluation device 100 evaluates the strange feeling, and outputs the strange feeling index (step S27).

As described above, by utilizing active learning for the collection of strange feeling labels, the workload of labeling by the domain expert can be reduced. Incidentally, in the work of giving the strange feeling labels described above, a so-called cloud sourcing may be utilized, and the strange feeling labels may be efficiently collected by the cooperation of a plurality of domain experts.

Modification 2

Although a binary label is used as the strange feeling label in the above-described example embodiment, a multi-valued label or a real value may be used. In the case of using a multi-valued label, a multi-valued classification method may be used for the strange feeling prediction model. In addition, when a real value is used, a regression classification method may be used for the strange feeling prediction model.

Modification 3

Regarding the collection of the strange feeling labels, when there are multiple domain experts, it is preferable to appropriately aggregate the answers to give the strange feeling labels according to the strong area and the weak area of each domain expert. In addition, if the persons who give the strange feeling labels includes experts and non-experts, the technology used for cloud sourcing or the like may be used to automatically find the persons who seem to be the experts, and the strange feeling labels may be obtained based on the answers of the experts.

Modified Example 4

If a white box model such as heterogeneous mixed learning is used as the strange feeling prediction model, humans can interpret the knowledge and empirical rules that the strange feeling prediction model acquired by the training. On the other hand, even when the strange feeling prediction model is a black box model, the basis for the prediction of the strange feeling can be presented to the user by utilizing the methods such as LIME (Local Interpretable Model-agnostic Explanations).

Modification 5

In the above-described example embodiment, supervised learning is performed using the strange feeling labels given by the domain experts. However, training of the strange feeling prediction model may be performed using semi-supervised learning using data without the strange feeling labels.

Modification 6

The strange feeling data may be collected at the time of operation of AI, and the above-described strange feeling prediction model may be appropriately updated. Specifically, when monitoring the system, the AI operator is enabled to record the strange feeling prediction. This enables training or updating of the strange feeling prediction model using the recorded strange feeling prediction data. In addition, by recording the strange feeling when the nature of the data being processed by the AI system changes, the collection cost of the strange feeling data can be reduced. In addition, the page viewing time when the AI operator confirms the prediction results by the system may be used as the strange feeling data. For example, the strange feeling data may be generated such that the strange feeling becomes larger as the page viewing time is longer.

APPLICATION EXAMPLES

The strange feeling evaluation method of the above example embodiment can be applied to the following.

Application Example 1: Application to Data Augmentation

Data augmentation is known as a technique to improve the accuracy of machine learning models. Data augmentation is a technique to improve the accuracy of the model by learning the model by increasing the data when the number of training data is not sufficient. However, it is necessary to properly augment the data according to the domain of the data.

For example, as the data augmentation for an image, enlargement, reduction, rotation, parallel translation, and clipping of the original image are known as a standard augmentation method. However, it is also known that it is not good to rotate the image too much, when data augmentation is carried out by the rotation. For example, in the case of a task of classifying numbers in an image, there is a disadvantage that the numbers "6" and "9" are confused by the rotation. As described above, the appropriate data augmentation method is different for the domains to which the data augmentation is applied. Therefore, it is necessary for the domain experts to verify which type of data augmentation method is appropriate for each domain. In such a case, it is possible to apply the strange feeling evaluation method according to the above example embodiment. That is, it is possible to carry out the evaluation of the data augmentation method by the domain experts using the strange feeling evaluation technique.

Specifically, the above diagnosis data prediction results z, $$z: \mathcal{D} \times \mathcal{G} \to \mathbb{R}^b \quad \text{[Formula 24]}$$

indicating the method of providing data to the domain experts is defined as the set of the augmentation methods. For example, in the case of data augmentation of an image, the data augmentation means presents the augmented data, in which the following data augmentation processing is applied to the original image, to the domain experts as the diagnosis data prediction result z.

Parallel translation: 10 pixels, 20 pixels, . . . 100 pixels
Rotation: 10 degrees, 20 degrees, . . . , 180 degrees
Zoom in/out: Zoom in ±10%, ±20%

The domain experts give the strange feeling labels to the processed image and the strange feeling prediction model is trained using the strange feeling labels. Thus, the trained strange feeling prediction model can judge the presence or absence of the strange feeling for each data augmentation method with the sense close to the domain experts. For example, in the above-described numeric classification of the image, the rotation close to 180 degrees is determined to have the strange feeling because it causes confusion between "6" and "9". Therefore, for example, if the data augmentation is performed using only the data augmentation method for which the strange feeling prediction model determines that there is no or small strange feeling, an appropriate data augmentation method can be employed for each domain.

Application Example 2: Application to Metamorphic Test

It is conceivable to apply the metamorphic testing, which is known as a test method of software, to the test of machine learning model. Metamorphic testing is a technique to confirm the consistency of the input/output relation of a function using the metamorphic relation. The metamorphic relation refers to the relation that "when a certain change is given to an input, the change in the output can be predicted theoretically."

Examples of metamorphic relationships include the following:
(i) When the function $f(x)=y$, there is "a" that does not change "y", such as $f(x+a)=y$.
(ii) When function $f(x)=y$, there is a function T where $f(T(x))=y$. Incidentally, the above example (i) corresponds to the case of $T(x)=x+a$.
(iii) Generally, when $f(x)=y$, if $f(T(x))=M(y; T)$, the function T and the function M are said to be in metamorphic relation, and the test is carried out using the function T and the function M.

However, since the metamorphic relationship changes depending on the data in the AI system, it is costly to determine the metamorphic relationship appropriately according to the data. Therefore, the strange feeling evaluation method of the above example embodiment is applied to determine an appropriate metamorphic relationship.

Specifically, first, the candidate acquisition means prepares a number of candidates of the function T and the function M that are assumed to be in the metamorphic relationship, and enumerates all of the functions M that can be used together with the function T. Here, the outputs of the function M and the function T correspond to the outputs of the aforementioned target prediction models. The n candidate sets are expressed as follows.

$$\{(T_i, M_i))\}_{i=1}^n$$ [Formula 25]

Next, for the prepared n candidates, $M(x)$ and $T(y_i;M)$ for a certain data $(x_j, y_j)$ are presented to the domain experts as $z_j=(M(x_i), T(y_i;M))$ (corresponding to the diagnosis data prediction results). For the output of the proposed $M(x_i)$ and $T(y_i;M)$, the domain experts assign the presence or absence of the strange feeling for the fact that the function T and the function M are metamorphically related, as the strange feeling labels. By training the strange feeling prediction model using these strange feeling labels, it is possible to generate a strange feeling prediction model that can evaluate the strange feeling with respect to the presence or absence of metamorphic relationships.

When the trained strange feeling prediction model can be generated in this way, $M(x_i)$ and $T(y_i;M)$ that are calculated for a set of $x_i$ and $y_i$ are inputted to the strange feeling prediction model. If the domain expert excludes the pairs of the function T and the function M having the strange feeling, only the pairs that are judged to have no strange feeling by the sense of domain experts remain. By performing the metamorphic testing using the remaining sets of the function T and the function M, the metamorphic testing fitted to the domain can be realized.

Second Example Embodiment

Figure 10:
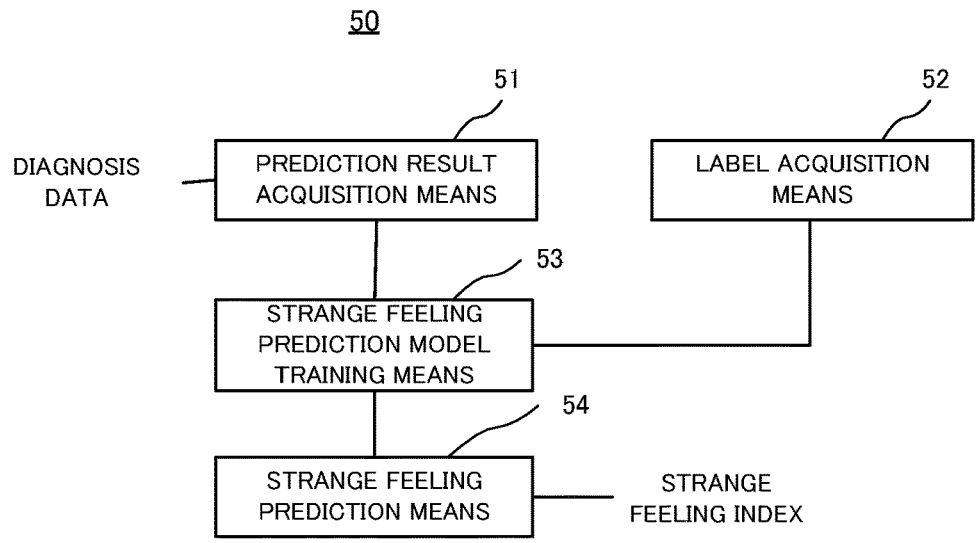
FIG. 10 is a block diagram showing a functional configuration of information processing according to a second example embodiment.

Next, a second example embodiment of the present invention will be described. FIG. 10 is a block diagram illustrating a functional configuration of an information processing device 50 according to the second example embodiment. The information processing device 50 includes a prediction result acquisition means 51, a label acquisition means 52, a strange feeling prediction model training means 53, and a strange feeling prediction means 54.

The prediction result acquisition means 51 inputs diagnosis data to a target prediction model which is a trained prediction model serving as a target, and acquires a prediction result by the target prediction model. The label acquisition means 52 acquires a strange feeling label indicating a strange feeling of an expert with respect to the prediction result. The strange feeling prediction model training means 53 trains a strange feeling prediction model using the prediction result and the strange feeling label. The strange feeling prediction means 54 outputs a strange feeling index indicating the strange feeling with respect to the prediction result outputted by the target prediction model, using the trained strange feeling prediction model.

Figure 11:
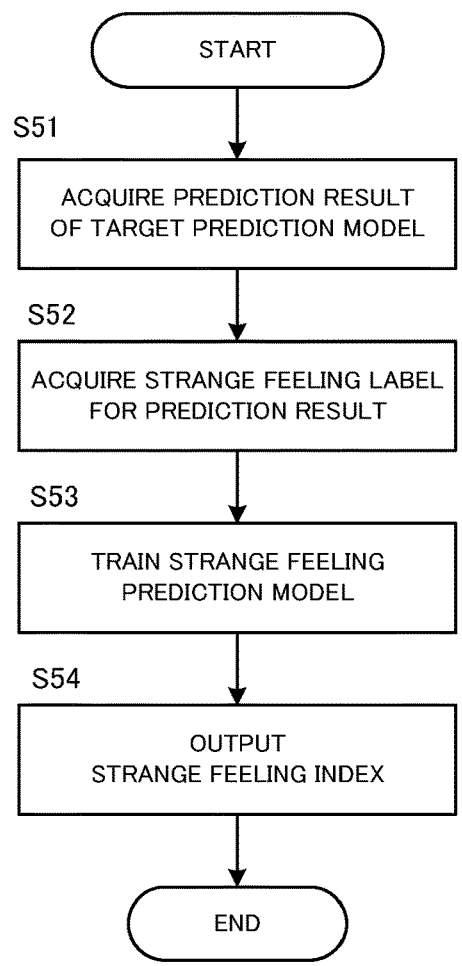
FIG. 11 is a flowchart of processing by the information processing device of the second example embodiment.

FIG. 11 is a flowchart of processing performed by the information processing device 50 according to the second example embodiment. The prediction result acquisition means 51 inputs diagnosis data to a target prediction model which is a trained prediction model serving as a target, and acquires a prediction result by the target prediction model (step S51). The label acquisition means 52 acquires a strange feeling label indicating a strange feeling of an expert with respect to the prediction result (step S52). The strange feeling prediction model training means 53 trains a strange feeling prediction model using the prediction result and the strange feeling label (step S53). The strange feeling prediction means 54 outputs a strange feeling index indicating the strange feeling with respect to the prediction result outputted by the target prediction model, using the trained strange feeling prediction model (step S54). By this, it becomes possible to evaluate the strange feeling for the prediction result by the target prediction model, from the viewpoint of the domain experts.

A part or all of the example embodiments described above may also be described as the following supplementary notes, but not limited thereto.

Supplementary Note 1
An information processing device comprising:
a prediction result acquisition means configured to input diagnosis data to a target prediction model which is a trained prediction model serving as a target, and acquire a prediction result by the target prediction model;
a label acquisition means configured to acquire a strange feeling label indicating a strange feeling of an expert with respect to the prediction result;
a strange feeling prediction model training means configured to train a strange feeling prediction model using the prediction result and the strange feeling label: and
a strange feeling prediction means configured to output a strange feeling index indicating the strange feeling with respect to the prediction result outputted by the target prediction model, using the trained strange feeling prediction model.

Supplementary Note 2
The information processing device according to Supplementary note 1,
wherein the label acquisition means sequentially acquires the strange feeling label for the diagnosis data, for which determination of whether or not there is a strange feeling is difficult, and
wherein the strange feeling prediction model training means repeats training or updating of the strange feeling prediction model using the acquired strange feeling label.

Supplementary Note 3
The information processing device according to Supplementary note 1 or 2, wherein the strange feeling prediction means outputs the strange feeling index for a plurality of target prediction models, and wherein the information processing device further comprises a model selection means configured to select one target prediction model whose strange feeling is smallest, from among the plurality of target prediction models, based on the strange feeling index.

Supplementary Note 4

The information processing device according to Supplementary note 1 or 2, further comprising a target prediction model training means configured to train the target prediction model such that the strange feeling is reduced by using a loss function including the strange feeling index as a regularization term.

Supplementary Note 5

The information processing device according to Supplementary note 1 or 2, further comprising:
- a target prediction model training means configured to train the target prediction model using training data: and
- a data augmentation means configured to generate augmented data based on the training data, wherein the strange feeling prediction means outputs the strange feeling index for the prediction result that the target prediction model outputted for the input of the augmented data, and wherein the data augmentation means determines whether or not to adopt the augmented data based on the strange feeling index.

Supplementary Note 6

The information processing device according to Supplementary note 1 or 2, further comprising a candidate acquisition means configured to acquire candidates of sets of a first function and a second function which is in metamorphic relationship with the first function, wherein the prediction result acquisition means acquires the outputs of the first function and the second function for the diagnosis data as the prediction results, and wherein the strange feeling prediction means outputs the strange feeling index indicating the strange feeling with respect to presence or absence of the metamorphic relationship between the first function and the second function, using the strange feeling prediction model.

Supplementary Note 7

An information processing method comprising:
- inputting diagnosis data to a target prediction model which is a trained prediction model serving as a target, and acquiring a prediction result by the target prediction model;
- acquiring a strange feeling label indicating a strange feeling of an expert with respect to the prediction result;
- training a strange feeling prediction model using the prediction result and the strange feeling label: and
- outputting a strange feeling index indicating the strange feeling with respect to the prediction result outputted by the target prediction model, using the trained strange feeling prediction model.

Supplementary Note 8

A recording medium recording a program, the program causing a computer to:
- input diagnosis data to a target prediction model which is a trained prediction model serving as a target, and acquire a prediction result by the target prediction model;
- acquire a strange feeling label indicating a strange feeling of an expert with respect to the prediction result;
- train a strange feeling prediction model using the prediction result and the strange feeling label: and
- output a strange feeling index indicating the strange feeling with respect to the prediction result outputted by the target prediction model, using the trained strange feeling prediction model.

While the present invention has been described with reference to the example embodiments and examples, the present invention is not limited to the above example embodiments and examples. Various changes which can be understood by those skilled in the art within the scope of the present invention can be made in the configuration and details of the present invention.

DESCRIPTION OF SYMBOLS

12 Processor
20 Predictor
30 Strange feeling predictor
50 Information processing device
100 Strange feeling evaluation device

What is claimed is:

1. An information processing device comprising:
a memory storing instructions; and
one or more processors configured to execute the instructions to:
input diagnosis data to a target prediction model serving as a target, and acquire a prediction result from the target prediction model;
acquire strange feeling labels indicating a strange feeling of an expert with respect to the prediction result;
train a strange feeling prediction model using the prediction result and the strange feeling labels so that the trained strange feeling prediction model is able to judge presence or absence of the strange feeling for each of a plurality of data augmentation methods respectively corresponding to the strange feeling labels;
output a strange feeling index indicating the strange feeling with respect to the prediction result outputted by the target prediction model, using the trained strange feeling prediction model; and
perform data augmentation using one of the plurality of data augmentation methods for which the trained strange feeling prediction model indicates that the strange feeling is small or none.

2. The information processing device according to claim 1,
wherein the one or more processors sequentially acquire the strange feeling labels for the diagnosis data, for which determination of whether or not there is a strange feeling is difficult, and
wherein the one or more processors repeat training or updating of the strange feeling prediction model using the acquired strange feeling labels.

3. The information processing device according to claim 1, wherein the one or more processors are further configured to train the target prediction model such that the strange feeling is reduced by using a loss function including the strange feeling index as a regularization term.

4. The information processing device according to claim 1, wherein the one or more processors are further configured to:
train the target prediction model using training data; and
generate augmented data based on the training data, wherein the one or more processors output the strange feeling index for the prediction result that the target prediction model output for the input of the augmented data, and wherein the one or more processors determine whether or not to adopt the augmented data based on the strange feeling index.

5. The information processing device according to claim 1, wherein the one or more processors are further configured to acquire candidates of sets of a first function and a second function in metamorphic relationship with the first function, wherein the one or more processors acquire outputs of the first function and the second function for the diagnosis data as the prediction result, and wherein the one or more processors output the strange feeling index indicating the strange feeling with respect to presence or absence of the metamorphic relationship between the first function and the second function, using the strange feeling prediction model.

6. An information processing method performed by a computer and comprising:

inputting diagnosis data to a target prediction model serving as a target, and acquire a prediction result from the target prediction model;

acquiring strange feeling labels indicating a strange feeling of an expert with respect to the prediction result;

training a strange feeling prediction model using the prediction result and the strange feeling labels so that the trained strange feeling prediction model is able to judge presence or absence of the strange feeling for each of a plurality of data augmentation methods respectively corresponding to the strange feeling labels;

outputting a strange feeling index indicating the strange feeling with respect to the prediction result outputted by the target prediction model, using the trained strange feeling prediction model; and performing data augmentation using one of the plurality of data augmentation methods for which the trained strange feeling prediction model indicates that the strange feeling is small or none.

7. A non-transitory computer-readable recording medium storing a program executable by a computer to perform processing comprising:

inputting diagnosis data to a target prediction model serving as a target, and acquire a prediction result from the target prediction model;

acquiring strange feeling labels indicating a strange feeling of an expert with respect to the prediction result;

training a strange feeling prediction model using the prediction result and the strange feeling labels so that the trained strange feeling prediction model is able to judge presence or absence of the strange feeling for each of a plurality of data augmentation methods respectively corresponding to the strange feeling labels;

outputting a strange feeling index indicating the strange feeling with respect to the prediction result outputted by the target prediction model, using the trained strange feeling prediction model; and performing data augmentation using one of the plurality of data augmentation methods for which the trained strange feeling prediction model indicates that the strange feeling is small or none.

\* \* \* \* \*